US012708270B2

(12) United States Patent
Yue et al.

(10) Patent No.: US 12,708,270 B2
(45) Date of Patent: Aug. 18, 2026

(54) MULTI-MODAL IMAGING DEVICE BASED ON RAMAN SPECTROSCOPY AND OPTICAL COHERENCE TOMOGRAPHY

(71) Applicants: BEIHANG UNIVERSITY, Beijing (CN); SUZHOU SURGI-MASTER HIGH TECH CO., LTD., Suzhou (CN)

(72) Inventors: Shuhua Yue, Beijing (CN); Shijie Zhu, Suzhou (CN); Xun Chen, Beijing (CN); Pu Wang, Beijing (CN)

(73) Assignees: BEIHANG UNIVERSITY, Beijing (CN); SUZHOU SURGI-MASTER HIGH TECH CO., LTD., Suzhou (CN)

( * ) Notice: Subject to any disclaimer, the term of this patent is extended or adjusted under 35 U.S.C. 154(b) by 183 days.

(21) Appl. No.: 18/670,798

(22) Filed: May 22, 2024

(65) Prior Publication Data

US 2024/0306921 A1 Sep. 19, 2024

Related U.S. Application Data

(63) Continuation of application No. PCT/CN2022/129303, filed on Nov. 2, 2022.

(30) Foreign Application Priority Data

Nov. 22, 2021 (CN) ......................... 202111381654.X

(51) Int. Cl.
*A61B 5/00* (2006.01)
*A61B 1/07* (2006.01)

(52) U.S. Cl.
CPC ............. *A61B 5/0075* (2013.01); *A61B 1/07* (2013.01); *A61B 5/0066* (2013.01)

(58) Field of Classification Search
CPC ....... A61B 5/0075; A61B 1/07; A61B 5/0066; A61B 5/0035
See application file for complete search history.

(56) References Cited

U.S. PATENT DOCUMENTS

| | | | | |
|---|---|---|---|---|
| 6,609,015 B2 * | 8/2003 | Lucassen | ............ | G02B 21/008 600/407 |
| 8,553,219 B2 * | 10/2013 | Patil | ......................... | G01J 3/44 356/73 |

(Continued)

FOREIGN PATENT DOCUMENTS

| | | |
|---|---|---|
| CN | 102147368 A | 8/2011 |
| CN | 112089404 A | 12/2012 |

(Continued)

OTHER PUBLICATIONS

International Search Report for corresponding International Patent Application No. PCT/CN2022/129303, mailed Jan. 20, 2023, 7 pages.

(Continued)

*Primary Examiner* — Sanjay Cattungal
(74) *Attorney, Agent, or Firm* — Cooper Legal Group, LLC

(57) ABSTRACT

The present disclosure provides a multi-modal imaging device based on Raman spectroscopy and optical coherence tomography. The multi-modal imaging device based on Raman spectroscopy and optical coherence tomography includes: a Raman spectroscopic analysis module configured to obtain Raman spectroscopic information of a target object on a first sampling position by using excitation light; an optical coherence tomography module configured to obtain at least one two-dimensional tissue structure image of the target object on a second sampling position by using imaging detection light; and a co-localization module configured to control the first sampling position of the excitation (Continued)

light in the Raman spectroscopic analysis module and/or the second sampling position in the optical coherence tomography module according to a determined concerned area of the target object, so that the first sampling position and the second sampling position are spatially co-localized in the concerned area.

18 Claims, 6 Drawing Sheets

(56) References Cited

U.S. PATENT DOCUMENTS 10,830,639 B2 * 11/2020 Urban ................ G02B 21/0064
2005/0283058 A1 * 12/2005 Choo-Smith ........ A61B 5/0088 356/73
2009/0021724 A1 * 1/2009 Mahadevan-Jansen .................... G01N 21/65 356/73
2013/0137944 A1 * 5/2013 Jeong .................. A61B 5/0068 600/431
2018/0270474 A1 * 9/2018 Liu ...................... A61B 5/0064
2022/0107487 A1 * 4/2022 Dennis .................. G01J 3/0229

FOREIGN PATENT DOCUMENTS

CN 112888934 A 6/2021
CN 113812928 A 12/2021
CN 113812929 A 12/2021
CN 114795120 A 7/2022

OTHER PUBLICATIONS

Ren, Xiaojing, et al., "Optical coherence tomography-guided confocal Raman microspectrometry for rapid measurements in tissues", Biomedical Optics Express, Jan. 1, 2022, 13(1): pp. 344-357.

* cited by examiner (a)

(b)

MULTI-MODAL IMAGING DEVICE BASED ON RAMAN SPECTROSCOPY AND OPTICAL COHERENCE TOMOGRAPHY

CROSS-REFERENCE TO RELATED APPLICATION

This application is a continuation of PCT application No. PCT/CN2022/129303, filed on Nov. 2, 2022, which claims the priority and benefit of Chinese patent application No. 202111381654.X, filed on Nov. 22, 2021. The entireties of PCT application No. PCT/CN2022/129303 and Chinese patent application No. 202111381654.X are hereby incorporated by reference herein and made a part of this specification.

TECHNICAL FIELD

The present disclosure relates to an optical imaging device for test/diagnosis, in particular to a multi-modal imaging device based on Raman spectroscopy and optical coherence tomography, in more particular to a multi-modal endoscope based on Raman spectroscopy and optical coherence tomography.

BACKGROUND

Early screening and test for cancers and postoperative reexamination are important means to improve a survival rate of patients, while endoscope imaging devices are important image diagnosis means for early screening and test for cancers and postoperative reexamination.

Optical coherence tomography (also known as optical coherence imaging, abbreviated as OCT) is an observation means for scattering light coherence imaging for physiological tissues. Optical coherence tomography has high spatial resolution, e.g., about 10 μm, which allows real-time non-invasive test for tissue scattering changes, provides two-dimensional or three-dimensional micrometer-scale tissue structures/morphological information, and achieves visual infiltration imaging. However, when used for early diagnosis for cancers, optical coherence tomography is not high in accuracy. For example, the sensitivity and specificity of optical coherence tomography for diagnosis of cervical intraepithelial neoplasia are only 88% and 69%.

Raman spectroscopy is an analysis means for obtaining information on aspects such as vibration and rotation of molecules by utilizing a Raman scattering effect of the molecules. Raman spectroscopy is related to molecular chemical bond information, and can recognize different types of molecules and evaluate relative concentration peaks according to different intensities. The accuracy and specificity of Raman spectroscopy for tumor diagnosis are higher than other methods. For example, the sensitivity of Raman spectroscopy for diagnosis of cervical intraepithelial neoplasia (CIN) is 93.5%, and the specificity is 97.8%; the sensitivity and specificity of Raman spectroscopy for diagnosis of early glioma are as high as 93% and 91%, respectively; and comparatively, the sensitivity and specificity of nuclear magnetic resonance diagnosis are only 88% and 54%, respectively. However, a Raman spectroscopic endoscope cannot provide a wide field-of-view imaging mode of a white light endoscope or a narrow-band endoscope and an optical coherence tomography, autofluorescence or confocal endoscope so as to be incapable of visually monitoring suspicious lesion areas during endoscopy.

Therefore, in order to improve the efficiency and accuracy of diagnosis/screening, it is expected that, on one hand, tissue structure image information (such as optical coherence tomographic information) can be obtained, and on the other hand, molecular structure information (such as Raman spectroscopic information) with high diagnosis sensitivity and specificity can also be obtained.

However, it is still not enough for diagnosis and screening to only obtain the two aspects of information due to a fact that the above-mentioned two aspects of information are often obtained from spatially-biased positions. That is to say, the above-mentioned two aspects of information represent different information of different areas (although the different areas may partially overlap), respectively. Therefore, when the above-mentioned two aspects of information are combined, it is easy to lower the accuracy of spatial information, which is not beneficial to providing meaningful auxiliary information for diagnosis/screening of cancers/tumors.

Thus, it can be seen that a new multi-modal imaging device based on Raman spectroscopy and optical coherence tomography is needed to solve the above-mentioned problems.

Besides, since a speed (such as higher than 100 frames/second) of optical coherence tomography is not matched with a speed (2-5 Hz) of Raman spectroscopy test, they cannot be combined together at a high efficiency. Obviously, due to the low speed of the Raman spectroscopy test, even if optical coherence tomography is combined with the Raman spectroscopy test, it still takes a relatively long time to obtain comprehensive information. Therefore, it is also expected to obtain tissue structure image information and Raman spectroscopic information at a higher speed.

Finally, it is also expected that a size of a probe of such a device is small enough (such as at least smaller than 10 mm) so as to be integrated with an existing endoscope system (such as a white light endoscope or a narrow-band endoscope).

SUMMARY

For solving the above-mentioned problems, the present disclosure provides a multi-modal imaging device based on Raman spectroscopy and optical coherence tomography. The multi-modal imaging device based on Raman spectroscopy and optical coherence tomography in the present disclosure includes a Raman spectroscopic analysis module, an optical coherence tomography module, and a co-localization module. According to the multi-modal imaging device based on Raman spectroscopy and optical coherence tomography in the present disclosure, the Raman spectroscopic analysis module and the optical coherence tomography module achieve imaging and test for a target object in the same co-localized area by using the co-localization module. Besides, the Raman spectroscopic analysis module and the optical coherence tomography module of the multi-modal imaging device in the present disclosure can cooperatively operate, thereby obtaining a diagnosis basis required for screening the target object (such as a cancer) at high efficiency, high accuracy and specificity. Due to the design of the multi-modal imaging device based on Raman spectroscopy and optical coherence tomography in the present disclosure, a probe is also allowed to be produced with a smaller size, which is beneficial to integration the probe into an existing endoscope system.

An embodiment of the present disclosure provides a multi-modal imaging device based on Raman spectroscopy and optical coherence tomography, including: a Raman spectroscopic analysis module configured to obtain Raman spectroscopic information of a target object on a first sampling position by using excitation light; an optical coherence tomography module configured to obtain at least one two-dimensional tissue structure image of the target object on a second sampling position by using imaging detection light; and a co-localization module configured to control the first sampling position of the excitation light in the Raman spectroscopic analysis module and/or the second sampling position in the optical coherence tomography module according to a determined concerned area of the target object, so that the first sampling position and the second sampling position are spatially co-localized in the concerned area.

According to the embodiment of the present disclosure, wherein the multi-modal imaging device based on Raman spectroscopy and optical coherence tomography includes a probe provided with a shell and a detection window and configured to detect the target object, and the excitation light from the Raman spectroscopic analysis module and the imaging detection light from the optical coherence tomography module are coupled in the probe.

According to the embodiment of the present disclosure, wherein the Raman spectroscopic analysis module includes a first light source, a first beam splitting mirror, a first coupling objective lens, a first optical fiber, a spectrometer, a first lens group, and a first dichroscope; the first beam splitting mirror is configured to transmit excitation light from the first light source and reflect Raman spectroscopy scattering signal light from the target object; the spectrometer is configured to receive the Raman spectroscopy scattering signal light from the target object reflected by the first beam splitting mirror; the first coupling objective lens is configured to receive emergent light from the first beam splitting mirror or the co-localization module; the first optical fiber is configured to receive emergent light from the first coupling objective lens; the first lens group is configured to receive emergent light from the first optical fiber; and the first dichroscope is configured to receive and transmit emergent light from the first lens group.

According to the embodiment of the present disclosure, wherein a grating and a receiving lens are arranged between the spectrometer and the first beam splitting mirror, the grating is configured to split reflected light from the first beam splitting mirror, the receiving lens is configured to receive emergent light from the grating, and the spectrometer is configured to receive emergent light from the receiving lens.

According to the embodiment of the present disclosure, wherein the first lens group includes a collecting lens.

According to the embodiment of the present disclosure, wherein the first optical fiber includes a multi-core optical fiber, a central fiber core group consisting of at least one fiber core on a central part of the multi-core optical fiber is configured to transmit Raman spectroscopy excitation light from the first light source, and peripheral fiber core groups consisting of at least one fiber core surrounding the central fiber core group in the multi-core optical fiber are configured to transmit the Raman spectroscopy scattering signal light.

According to the embodiment of the present disclosure, wherein the peripheral fiber core groups are symmetrically distributed with the central fiber core group as a center.

According to the embodiment of the present disclosure, wherein a band-pass fiber is arranged on a tail end of a side, close to the target object, of the central fiber core group, and notch filters and/or long pass filters are arranged on tail ends of sides, close to the target object, of the peripheral fiber core groups.

According to the embodiment of the present disclosure, wherein cross sections of the central fiber core group and the peripheral fiber core groups are basically round.

According to the embodiment of the present disclosure, wherein the optical coherence tomography module includes a detector, a second light source, a beam splitter, an interferometer, a coupling optical fiber, a second optical fiber, a second lens group, a proximal scanning sub-module, and a first reflecting mirror; the second light source, the interferometer, the detector and the second optical fiber are optically coupled to the beam splitter via a part of the coupling optical fiber; the other part of the coupling optical fiber is coupled to the second optical fiber; the second lens group is configured to receive emergent light from the second optical fiber, the first reflecting mirror is configured to reflect emergent light from the second lens group, and the first dichroscope is configured to reflect reflected light from the first reflecting mirror, so that light from the first lens group is coupled with light from the second lens group; and the proximal scanning sub-module is configured to control a position of the first reflecting mirror.

According to the embodiment of the present disclosure, wherein the first lens group and the second lens group are arranged in parallel in the probe, and the first dichroscope, the proximal scanning sub-module, the first reflecting mirror and at least one part of the second optical fiber are arranged in the probe.

According to the embodiment of the present disclosure, the proximal scanning sub-module is configured to control imaging detection light from the second light source by controlling the position of the first reflecting mirror so as to obtain a position of the tissue structure image of the target object.

According to the embodiment of the present disclosure, wherein the proximal scanning sub-module includes a micromotor.

According to the embodiment of the present disclosure, wherein the second lens group includes a second focusing lens and a diffraction lens, and the diffraction lens is arranged between the second focusing lens and the first reflecting mirror.

According to the embodiment of the present disclosure, wherein the second optical fiber or the coupling optical fiber includes a single-mode optical fiber.

According to the embodiment of the present disclosure, wherein the optical coherence tomography module includes a detector, a second light source, a beam splitter, an interferometer, a coupling optical fiber, a remote scanning sub-module, a first reflecting mirror, a second coupling objective lens, a second optical fiber, a second lens group, and a second reflecting mirror; wherein the beam splitter, the remote scanning sub-module, the first reflecting mirror, the second coupling objective lens and the second optical fiber are sequentially arranged in a transmission direction of emergent light from the second light source; the second light source, the interferometer, the detector and the remote scanning sub-module are optically coupled to the beam splitter via the coupling optical fiber; the remote scanning sub-module is arranged between the first reflecting mirror and the beam splitter and is configured to receive and reflect light from the second light source and transmitted by the beam splitter; the second coupling objective lens is configured to receive light reflected by the first reflecting mirror; the second optical fiber is configured to receive emergent light from the second coupling objective lens; and the second lens group is configured to receive emergent light from the second optical fiber, the second reflecting mirror is configured to reflect emergent light from the second lens group, and the first dichroscope is configured to reflect reflected light from the second reflecting mirror, so that light from the first lens group is coupled with light from the second lens group.

According to the embodiment of the present disclosure, wherein the first lens group and the second lens group are arranged in parallel in the probe, and the first dichroscope, the second reflecting mirror and at least one part of the second optical fiber are arranged in the probe.

According to the embodiment of the present disclosure, wherein the remote scanning sub-module is configured to control imaging detection light from the second light source by rotating around at least one axis so as to obtain a position of the tissue structure image of the target object.

According to the embodiment of the present disclosure, wherein the remote scanning sub-module includes a Galvo galvanometer, an MEMS-driven reflecting mirror or a resonant galvanometer.

According to the embodiment of the present disclosure, wherein the second optical fiber includes a multi-core optical fiber.

According to the embodiment of the present disclosure, wherein the second lens group includes a second focusing lens and a diffraction lens, and the diffraction lens is arranged between the second focusing lens and the second reflecting mirror.

According to the embodiment of the present disclosure, wherein the second optical fiber or the coupling optical fiber includes a single-mode optical fiber.

According to the embodiment of the present disclosure, wherein the co-localization module is arranged in an incident light path of the excitation light from the Raman spectroscopic analysis module.

According to the embodiment of the present disclosure, wherein the co-localization module is arranged between the first beam splitting mirror and the first coupling objective lens.

According to the embodiment of the present disclosure, wherein the co-localization module has a first mode and a second mode which are switchable; in the first mode, the co-localization module does not change the first sampling position; and in the second mode, the co-localization module is configured to control the first sampling position.

According to the embodiment of the present disclosure, wherein the co-localization module includes a first flip mirror, a second flip mirror, a first scanning galvanometer, and a second scanning galvanometer; the first flip mirror and the second flip mirror are arranged between the first beam splitting mirror and the first coupling objective lens; the first flip mirror and the second flip mirror are configured to control mirror surfaces of the first flip mirror and the second flip mirror to be parallel or not parallel to a light path between the first beam splitting mirror and the first coupling objective lens by rotating around an axis orthogonal to the light path between the first beam splitting mirror and the first coupling objective lens; and the first scanning galvanometer and the second scanning galvanometer are configured to control the first sampling position by rotating around different axes; wherein in the first mode, the mirror surfaces of the first flip mirror and the second flip mirror are parallel to the light path between the first beam splitting mirror and the first coupling objective lens; and in the second mode, the mirror surfaces of the first flip mirror and the second flip mirror are not parallel to the light path between the first beam splitting mirror and the first coupling objective lens.

According to the embodiment of the present disclosure, wherein in the second mode, the first flip mirror is configured to receive and reflect light transmitted by the first beam splitting mirror, the first scanning galvanometer is configured to receive and reflect reflected light from the first flip mirror, the second scanning galvanometer is configured to receive and reflect reflected light from the first scanning galvanometer, the second flip mirror is configured to receive and reflect reflected light from the second scanning galvanometer, and the first coupling objective lens is configured to receive reflected light from the second flip mirror.

According to the embodiment of the present disclosure, wherein each of the first scanning galvanometer and the second scanning galvanometer includes a Galvo galvanometer, an MEMS-driven reflecting mirror or a resonant galvanometer.

According to the embodiment of the present disclosure, wherein the co-localization module is configured to move the first sampling position to overlap with a position of the concerned area.

According to the embodiment of the present disclosure, wherein the first lens group is configured to enable a light spot of the excitation light from the Raman spectroscopic analysis module on the first sampling position basically overlaps with the concerned area.

According to the embodiment of the present disclosure, wherein the multi-modal imaging device based on Raman spectroscopy and optical coherence tomography is an endoscope.

According to the embodiment of the present disclosure, wherein a diameter of the probe is 2-10 mm.

According to the embodiment of the present disclosure, wherein a diameter of the probe is 2-5 mm.

According to the embodiment of the present disclosure, wherein the multi-modal imaging device further includes an image processing module configured to fuse the Raman spectroscopic information of the first sampling position and the at least one two-dimensional tissue structure image of the second sampling position, which are spatially co-localized, so as to generate fused multi-modal information of the concerned area.

According to the multi-modal imaging device based on Raman spectroscopy and optical coherence tomography in the present disclosure, the Raman spectroscopic analysis module and the optical coherence tomography module can detect/test the same area by using the co-localization module so as to obtain the tissue structure image and the Raman spectroscopic information which are spatially co-localized.

In addition, according to the multi-modal imaging device provided by the present disclosure, the Raman spectroscopic analysis module and the optical coherence tomography module can also cooperatively operate in a high-efficiency mode by using the co-localization module. Therefore, during the diagnosis of cancers and other diseases, the advantages of the accuracy and specificity of the Raman spectroscopic analysis module and the advantage that the optical coherence tomography module two-dimensionally or three-dimensionally obtains the tissue structure information with high spatial resolution can be used at the same time, and at the same time, the problem that the speed of Raman spectroscopy test is lower than the speed of optical coherence tomography is avoided. The multi-modal imaging device provided by the present disclosure also achieves spatial co-localization of Raman spectroscopic analysis and optical coherence tomography, thereby achieving precise test for the target object (such as a tumor or a cancer).

BRIEF DESCRIPTION OF THE DRAWINGS

To describe the technical solutions in the embodiments of the present disclosure more clearly, the accompanying drawings required for describing the embodiments will be briefly introduced below. Apparently, the accompanying drawings in the following description show only some exemplary embodiments of the present disclosure, and those of ordinary skill in the art may still derive other accompanying drawings from these accompanying drawings without creative efforts.

DETAILED DESCRIPTION

Figure 1:
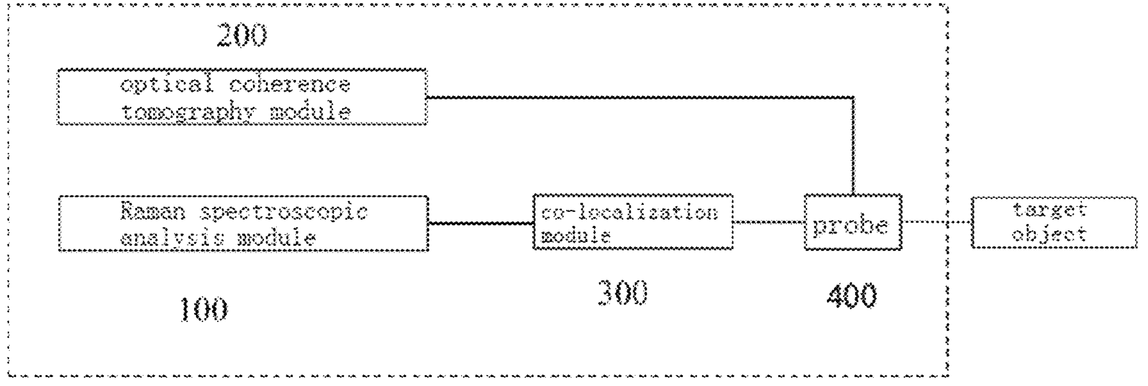
FIG. 1 shows a schematic diagram of a multi-modal imaging device based on Raman spectroscopy and optical coherence tomography according to an embodiment of the present disclosure.

In order to make objectives, technical solutions and advantages of the present disclosure more obvious, the exemplary embodiments of the present disclosure will be described below with reference to detailed description for the accompanying drawings. Apparently, the described embodiments are only a part of the embodiments of the present disclosure, not all the embodiments. It should be understood that the present disclosure is not limited by the exemplary embodiments described herein.

In the present description and the accompanying drawings, the basically same or similar steps and elements are represented by the same or similar reference numerals in the accompanying drawings, and repeated description for these steps and elements will be omitted. At the same time, in the description of the present disclosure, terms "first", "second" and the like are only for descriptive purposes, but cannot be understood as indicating or implying the relative importance or order.

In the present description and the accompanying drawings, elements are described in a singular or plural form according to embodiments. However, the singular or plural form is appropriately selected for the proposed situation, which is only intended to facilitate explanation, rather than to limit the present disclosure thereto. Therefore, the singular form may include the plural form, and the plural form may also include the singular form unless it is explicitly described in the context otherwise.

In the prior art, it is known that a target object (such as a cancer/tumor) is diagnosed/screened by using Raman spectroscopy or optical coherence tomography. However, either of the technologies has its own defects when used for screening, and high efficiency, high accuracy and high specificity cannot be achieved at the same time. Especially, since Raman spectroscopy test is relatively slow, and information obtained by using Raman spectroscopy and optical coherence tomography at the same time is information in different areas, it is easy to lower the accuracy of spatial information when the above-mentioned obtained information is combined, which is not beneficial to providing meaningful auxiliary information for diagnosis/screening of cancers/tumors.

In order to solve the above-mentioned technical problem, the present disclosure provides a multi-modal imaging device based on Raman spectroscopy and optical coherence tomography. In addition to a Raman spectroscopic analysis module and an optical coherence tomography module, the multi-modal imaging device based on Raman spectroscopy and optical coherence tomography further includes a co-localization module which can control sampling positions where a target object is detected by the Raman spectroscopic analysis module and/or the optical coherence tomography module. Therefore, by controlling the sampling positions for detecting the target object, the multi-modal imaging device in the present disclosure can achieve spatial co-localization detection based on Raman spectroscopy and optical coherence tomography. Besides, the multi-modal imaging device provided by the present disclosure can also reduce areas required to be detected for Raman spectroscopic analysis, that is to say, it is unnecessary to perform Raman spectroscopic analysis on all areas, but only a concerned area in an image obtained by the optical coherence tomography module is analyzed. For example, it is only necessary to control a first sampling position of Raman spectroscopy by the co-localization module, thereby analyzing the concerned area in the image obtained by the optical coherence tomography module, in this way, defects of low speed of Raman spectroscopic analysis test are avoided to a great extent, the advantages of high accuracy and high specificity of Raman spectroscopic analysis are still utilized, and then, the overall test efficiency is increased in a cooperative mode. Obviously, in such a mode, two kinds of information for spatial co-localization are also obtained. In the multi-modal imaging device based on Raman spectroscopy and optical coherence tomography in the present disclosure, focusing lenses are arranged in a probe, so that a size of the probe can be reduced, which is beneficial to integration to an existing endoscope system.

The above-mentioned multi-modal imaging device based on Raman spectroscopy and optical coherence tomography in the present disclosure will be described in detail below with reference to the accompanying drawings.

FIG. 1 shows a schematic diagram of a multi-modal imaging device based on Raman spectroscopy and optical coherence tomography according to an embodiment of the present disclosure.

Refer to FIG. 1, the multi-modal imaging device based on Raman spectroscopy and optical coherence tomography may include a Raman spectroscopic analysis module 100, an optical coherence tomography module 200, and a co-localization module 300.

The multi-modal imaging device based on Raman spectroscopy and optical coherence tomography may further include a probe 400.

The Raman spectroscopic analysis module 100 may be configured to obtain Raman spectroscopic information of a target object on a first sampling position by using excitation light. The optical coherence tomography module 200 may be configured to obtain at least one two-dimensional tissue structure image of the target object on a second sampling position by using imaging detection light.

The co-localization module 300 may be configured to control the first sampling position of the excitation light in the Raman spectroscopic analysis module and/or the second sampling position in the optical coherence tomography module according to a determined concerned area of the target object, so that the first sampling position and the second sampling position are spatially co-localized in the concerned area. Refer to FIG. 1, a light path of the Raman spectroscopy excitation light from the Raman spectroscopic analysis module 100 and passing through the co-localization module 300 and a light path of the imaging detection light from the optical coherence tomography module 200 probe and detect the target object after coupled in the probe 400.

In an implementation according to FIG. 1, the concerned area (such as a possible lesion area in a body of a patient) of the target object is obtained by an imaging device (not shown, such as a white light endoscope module and/or a narrow-band imaging module of an endoscope) different from the multi-modal imaging device.

In an embodiment, for example, in an image of the target object obtained by the white light endoscope module and/or the narrow-band imaging module of the endoscope, a predetermined area can be determined as the concerned area of the target object by manual operation from a doctor.

In another embodiment, in the image of the target object obtained by the white light endoscope module and/or the narrow-band imaging module of the endoscope, the predetermined area can also be determined as the concerned area of the target object by a processing module of the multi-modal imaging device according to a predetermined image processing algorithm.

The co-localization module 300 is configured to control the first sampling position of the excitation light in the Raman spectroscopic analysis module 100 to move to basically overlap with the concerned area; the optical coherence tomography module 200 is configured to perform imaging detection on the first sampling position (i.e., the concerned area), so that the first sampling position and the second sampling position (from the optical coherence tomography module 200) are spatially co-localized in the concerned area. However, the present disclosure is not limited to such a specific implementation. For example, although it is not shown, the co-localization module 300 in the present disclosure may also control the second sampling position of the optical coherence tomography module 200 to move to basically overlap with the concerned area, and the sampling position is analyzed and detected by using the Raman spectroscopic analysis module 100, so that spatial co-localization is achieved in the concerned area. In addition, the implementation of the present disclosure may further include that the first sampling position and the second sampling position are controlled simultaneously and/or synchronously to scan, analyze and detect the concerned area.

In another implementation according to FIG. 1, the optical coherence tomography module 200 may be configured to obtain at least one two-dimensional tissue structure image of the target object by using imaging detection light and determine the concerned area of the target object in the at least one two-dimensional tissue structure image, and the co-localization module 300 may be configured to control the (first) sampling position of the excitation light in the Raman spectroscopic analysis module 100 according to the determined concerned area, thereby obtaining Raman spectroscopic information of different positions in the concerned area. However, the present disclosure is not limited thereto. For example, although it is not shown, the Raman spectroscopic analysis module 100 may also be used to determine the concerned area of the target object and control the second sampling position of the optical coherence tomography module 200 to be scanned for imaging in the concerned area, thereby obtaining a tissue structure image and axial information in the concerned area. Obviously, no matter whether the first sampling position of the Raman spectroscopic analysis module 100 or the second sampling position of the optical coherence tomography module 200, the Raman spectroscopic information and the tissue structure image which are spatially co-localized can be obtained in the present disclosure by using the co-localization module 300. The skilled in the art can adopt a corresponding implementation based on an actual situation.

A relationship among all the modules in FIG. 1 is only illustrative, and is not intended to limit a specific control mode and a specific connection relationship of the co-localization module 300.

It can be seen from FIG. 1 that the co-localization module 300 makes operating personnel capable of controlling the first sampling position of the Raman spectroscopy excitation light, so that the first sampling position basically overlaps with the concerned area, then, the second sampling position covers (such as by scanning) the first sampling position, in this way, the Raman spectroscopic information and a tissue structure/morphological image which are spatially co-localized can be obtained. Besides, in a variant implementation, the optical coherence tomography module 200 can rapidly obtain tissue structure image and determine the concerned area of the target object, and then further guide the sampling position of the Raman spectroscopy excitation light, thereby obtaining diagnosis information with high accuracy and specificity on a high-risk position of the target object.

Contents included by all the modules in FIG. 1 will be described in detail below in conjunction with FIG. 2 and FIG. 5B.

Figure 2:
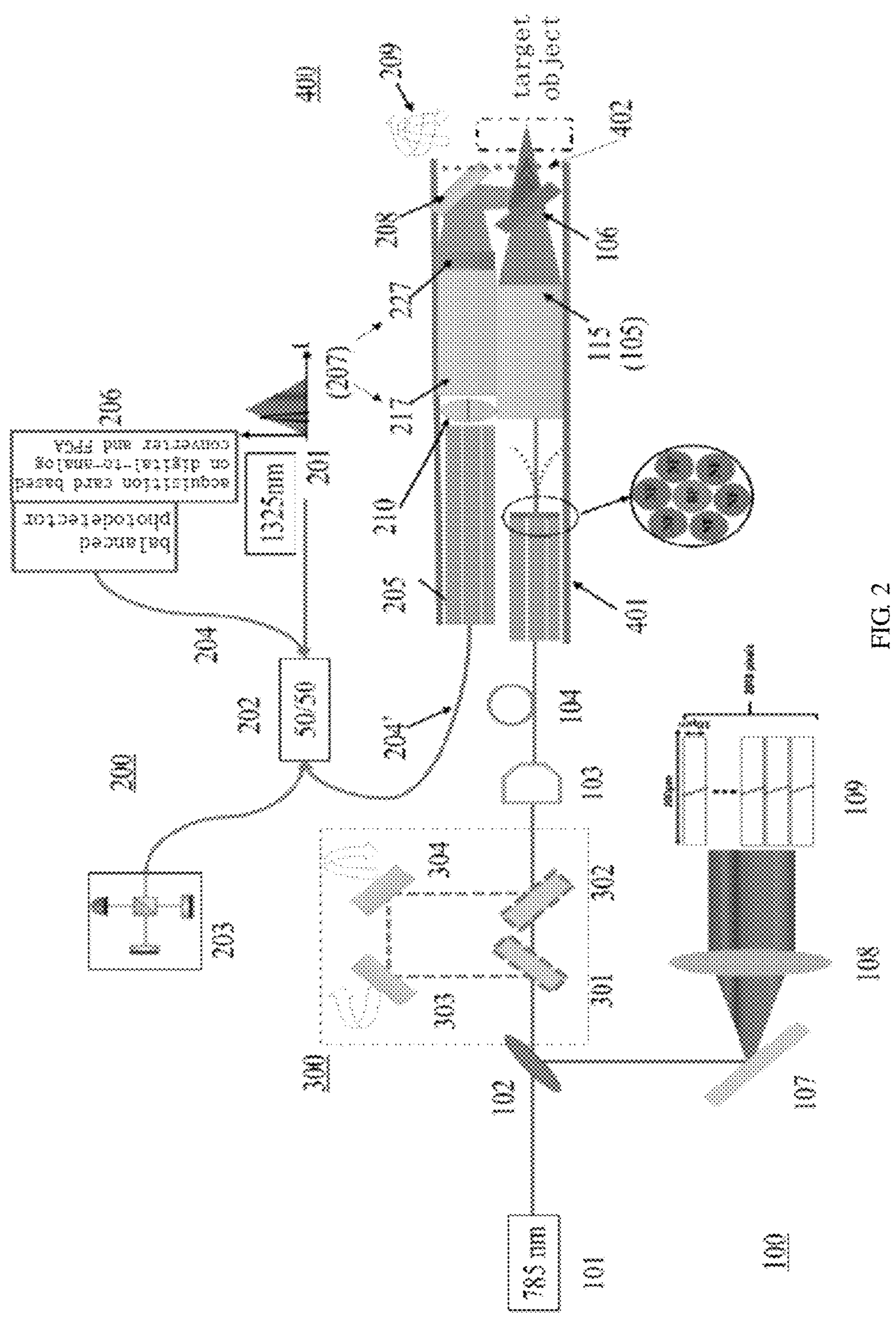
FIG. 2 shows a schematic diagram of a multi-modal imaging device based on Raman spectroscopy and optical coherence tomography according to an implementation of an embodiment of the present disclosure.

FIG. 2 shows a schematic diagram of a multi-modal imaging device based on Raman spectroscopy and optical coherence tomography according to an implementation of an embodiment of the present disclosure.

Refer to FIG. 2, the probe 400 included by the multi-modal imaging device based on Raman spectroscopy and optical coherence tomography may be provided with a shell 401 and a detection window 402 and configured to detect the target object, and the excitation light from the Raman spectroscopic analysis module 100 and the imaging detection light from the optical coherence tomography module 200 are coupled in the probe 400.

The Raman spectroscopic analysis module 100 may include a first light source 101, a first beam splitting mirror 102, a first coupling objective lens 103, a first optical fiber 104, a spectrometer 109, a first lens group 105, and a first dichroscope 106; and the first beam splitting mirror 102, the co-localization module 300, the first coupling objective lens 103, the first optical fiber 104, the first lens group 105 and the first dichroscope 106 are respectively arranged on an emergent light path of the Raman spectroscopy excitation light.

The first light source 101 may select any light source applicable to the Raman spectroscopy excitation light in the art, for example, a Raman excitation light source of which a wavelength is 785 nm is used in an implementation shown in FIG. 2.

The first beam splitting mirror 102 may be configured to transmit excitation light from the first light source 101 and reflect Raman spectroscopy scattering signal light from the target object.

The spectrometer 109 may be configured to receive the Raman spectroscopy scattering signal light reflected by the first beam splitting mirror 102 and from the target object.

The first coupling objective lens 103 is configured to receive emergent light from the first beam splitting mirror 102 or the co-localization module 300.

The first optical fiber 104 may be configured to receive emergent light from the first coupling objective lens 103.

The first lens group 105 may be configured to receive emergent light from the first optical fiber 104.

The first dichroscope 106 may be configured to receive and transmit emergent light from the first lens group 105.

A grating 107 and a receiving lens 108 are arranged between the spectrometer 109 and the first beam splitting mirror 102.

The grating 107 may be configured to split reflected light from the first beam splitting mirror 102.

The receiving lens 108 may be configured to receive emergent light from the grating 107.

The spectrometer 109 may be configured to receive emergent light from the receiving lens 108.

The first lens group 105 may include a collective lens 115.

By adjusting parameters of the collective lens 115, a size of a light spot of Raman spectroscopy on the target object can be controlled. As required, the size of the light spot can be adjusted within a range from 5 μm to 1 mm (diameter). In a preferred implementation, by using the collective lens 115, the size of the light spot of the Raman spectroscopy excitation light from the first light source 101 is basically the same as the size of the concerned area. In addition, in an alternative implementation, the first lens group may also adopt a focusing lens including a focusing lens with high dispersion and/or a high numerical aperture. For example, a usable focusing lens has an effective focal length of 2-3 mm, a working distance of 1 mm, and a numerical aperture expressed as N/A=0.5. The lens with high dispersion can increase an axial field of view, and the high numerical aperture is beneficial to the improvement of a resolution and an imaging signal-to-noise ratio. In this implementation of the present disclosure, by using the collective lens 115, the size of the light spot of the Raman spectroscopy excitation light from the first light source 101 is consistent with the size of the concerned area, which is preferable due to the conservation of time for obtaining the Raman spectroscopic information.

At the same time, splitting light by using the lens with high dispersion and the gratin is beneficial to obtaining Raman spectroscopic information of different depths of the target object at the same time and improving the test speed.

The first optical fiber 104 may include a multi-core optical fiber, wherein a central fiber core group consisting of at least one fiber core on a central part of the multi-core optical fiber is configured to transmit Raman spectroscopy excitation light from the first light source 101, and peripheral fiber core groups consisting of at least one fiber core surrounding the central fiber core group in the multi-core optical fiber are configured to transmit the Raman spectroscopy scattering signal light.

The peripheral fiber core groups may be symmetrically distributed with the central fiber core group as a center.

A band-pass fiber is arranged on a tail end of a side, close to the target object, of the central fiber core group, and notch filters and/or long pass filters are arranged on tail ends of sides, close to the target object, of the peripheral fiber core groups.

Cross sections of the central fiber core group and the peripheral fiber core groups are basically round.

Figure 3:
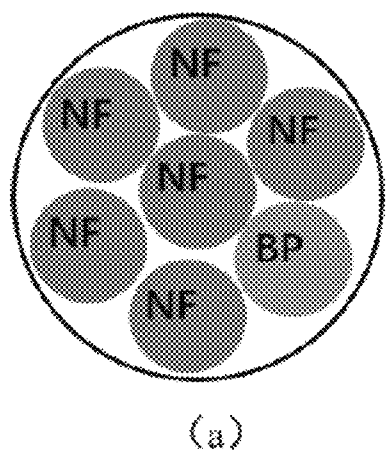
FIG. 3 shows a layout mode of a multi-core optical fiber included by a first optical fiber according to an embodiment of the present disclosure.
Figure 3:
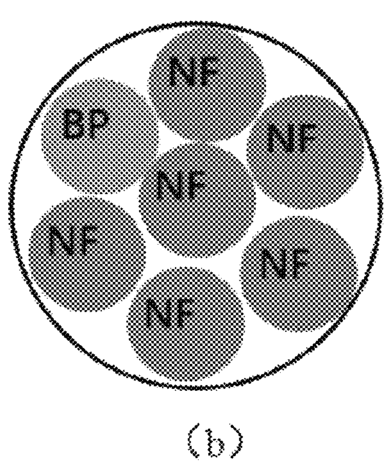

As shown in FIG. 2, the enlarging of a cross section of a side, close to the target object, of the first optical fiber 104 is schematically described, wherein one layout mode of the multi-core optical fiber included in the first optical fiber is only shown, and more other layout modes refer to FIG. 3. Besides, such a centrosymmetric layout mode shown in FIG. 2 is beneficial to reducing the signal loss to the greatest extent and obtaining a Raman spectroscopy signal with a high signal-to-noise ratio.

The central fiber core group (such as a central fiber core group consisting of a fiber core corresponding to a sign "BP" in FIG. 2) located in the probe 400 and consisting of the at least one fiber core on the central part of the multi-core optical fiber is configured to transmit the Raman spectroscopy excitation light from the first light source 101, and the peripheral fiber core groups (such as peripheral fiber core groups consisting of fiber cores corresponding to a sign "NF" in FIG. 2) consisting of the at least one fiber core surrounding the central fiber core group in the multi-core optical fiber are configured to transmit the Raman spectroscopy scattering signal light, wherein the cross sections of the central fiber core group and the peripheral fiber core groups are preferably round.

The band-pass (BP) fiber represented by BP is arranged on the tail end of the side, close to the target object, of the central fiber core group, and the notch filters (NF) represented by NF are arranged on the tail ends of the sides, close to the target object, of the peripheral fiber core groups. That is to say, the Raman spectroscopy excitation light excites Raman spectroscopy of the target object through the band-pass filter, a Raman scattering light signal filters background noise through the notch filters, and such settings are beneficial to increasing the signal-to-noise ratio of the signal.

As shown in FIG. 2, the optical coherence tomography module 200 may include a detector 206, a second light source 201, a beam splitter 202, an interferometer 203, a coupling optical fiber 204, a second optical fiber 205, a second lens group 207, a proximal scanning sub-module 209, and a first reflecting mirror 208.

The second light source 201 may select any light source applicable to optical coherence tomography in the art, for example, a swept light source of which a wavelength is 1325 nm is used in an implementation shown in FIG. 2.

The detector 206 may include a balanced photodetector and an acquisition system based on a high-speed digital-to-analog converter and a Field Programmable Gate Array (FPGA), which can achieve tissue structure image reconstruction and display of a video flow. An FPGA system converts a detection light interference signal into a sample structure grayscale map and an attenuation coefficient grayscale map which are transmitted to an upper computer so as to be displayed.

The beam splitter 202 may be a 50/50 beam splitter as shown in the figure.

A circulator (not shown) may be arranged between the detector 206 and the beam splitter 202.

The second light source 201, the interferometer 203, the detector 206 and the second optical fiber 205 are optically coupled to the beam splitter 202 via a part of the coupling optical fiber 204.

The other part 204' of the coupling optical fiber 204 is coupled to the second optical fiber 205.

The second lens group 207 may be configured to receive emergent light from the second optical fiber 205, the first reflecting mirror 208 may be configured to reflect emergent light from the second lens group 207, and the first dichroscope 106 may be configured to reflect reflected light from the first reflecting mirror 208, so that light from the first lens group 105 is coupled with light from the second lens group 207.

The first lens group 105 and the second lens group 207 may be arranged in parallel in the probe 400, and the first dichroscope 106, the proximal scanning sub-module 209, the first reflecting mirror 208 and at least one part of the second optical fiber 205 may be arranged in the probe 400. By such a design of the probe, an internal diameter of the probe can be reduced to 2-10 mm (which is much smaller than the size of 5 cm used in a traditional light path design in the prior art), which is beneficial to integration into a working channel of an existing endoscope system to reduce damage possibly brought by endoscope detection, thereby being beneficial to clinical application.

The proximal scanning sub-module 209 may be configured to control a position of the first reflecting mirror 208.

The proximal scanning sub-module 209 may be configured to control imaging detection light from the second light source 201 by controlling the position of the first reflecting mirror 208 so as to obtain a position of the tissue structure image of the target object.

The proximal scanning sub-module 209 may include a micromotor, wherein the micromotor may rotate around at least one axis (such as x axis and/or y axis) to achieve rapid two-dimensional scanning (i.e., line-by-line scanning, one two-dimensional tissue structure image is obtained by scanning every time) for the target object, thereby obtaining at least one two-dimensional tissue structure image of the target object; and when the target object is scanned to obtain a plurality of two-dimensional tissue structure images, a three-dimensional view of the target object can be formed.

The second lens group 207 may include a second focusing lens 217 and a diffraction lens 227, wherein the diffraction lens 227 may be arranged between the second focusing lens 217 and the first reflecting mirror 208.

A coupling adhesive 210 may be arranged between the second optical fiber 205 and the second focusing lens 217, wherein the coupling adhesive 210 may be configured to better couple a light path between the second optical fiber 205 and the second focusing lens 217 so as to better transmit light. It is noted that the coupling adhesive 210 is not necessarily arranged, but is preferably arranged.

By using the second focusing lens 217, a size of a light spot of incident light emitted by the second light source 201 can be controlled. As required, the size of the light spot can be adjusted within a range from 5 μm to 1 mm (diameter). In addition, a usable focusing lens includes a focusing lens with high dispersion and/or a high numerical aperture. For example, the usable focusing lens has an effective focal length of 2-3 mm, a working distance of 1 mm, and a numerical aperture expressed as N/A=0.5. The lens with high dispersion can increase an axial field of view, and the high numerical aperture is beneficial to the improvement of a resolution and an imaging signal-to-noise ratio. In addition, in this implementation of the present disclosure, the diffraction lens 227 can compensate the dispersion, improve a wavelength and a bandwidth, and improve the resolution, thereby improving the imaging quality.

The second optical fiber 205 or the coupling optical fiber 204 may include a single-mode optical fiber.

Further refer to FIG. 2, the co-localization module 300 may be arranged in an incident light path of the excitation light from the Raman spectroscopic analysis module 100.

The co-localization module 300 may be arranged between the first beam splitting mirror 102 and the first coupling objective lens 103.

The co-localization module 300 may 300 may have a first mode and a second mode which are switchable; wherein in the first mode, the co-localization module 300 does not change the first sampling position; and in the second mode, the co-localization module 300 may be configured to control the first sampling position.

The co-localization module 300 may include a first flip mirror 301, a second flip mirror 302, a first scanning galvanometer 303, and a second scanning galvanometer 304, wherein the first flip mirror 301 and the second flip mirror 302 may be arranged between the first beam splitting mirror 102 and the first coupling objective lens 103.

The first flip mirror 301 and the second flip mirror 302 may be configured to control mirror surfaces of the first flip mirror 301 and the second flip mirror 302 to be parallel or not parallel to a light path between the first beam splitting mirror 102 and the first coupling objective lens 103 by rotating around an axis orthogonal to the light path between the first beam splitting mirror 102 and the first coupling objective lens 103; and the first scanning galvanometer 303 and the second scanning galvanometer 304 may be configured to control the first sampling position by rotating around different axes.

In the first mode, the mirror surfaces of the first flip mirror 301 and the second flip mirror 302 are parallel to the light path between the first beam splitting mirror 102 and the first coupling objective lens 103.

In the second mode, the mirror surfaces of the first flip mirror 301 and the second flip mirror 302 are not parallel to the light path between the first beam splitting mirror 102 and the first coupling objective lens 103.

In the second mode, the first flip mirror 301 may be configured to receive and reflect light transmitted by the first beam splitting mirror 102, the first scanning galvanometer 303 may be configured to receive and reflect reflected light from the first flip mirror 301, the second scanning galvanometer 304 may be configured to receive and reflect reflected light from the first scanning galvanometer 303, the second flip mirror 302 may be configured to receive and reflect reflected light from the second scanning galvanometer 304, and the first coupling objective lens 103 may be configured to receive reflected light from the second flip mirror 302.

Each of the first scanning galvanometer 303 and the second scanning galvanometer 304 may include a Galvo galvanometer (a Galvo scanning system), a Micro-Electro-Mechanical System (MEMS)-driven reflecting mirror or a resonant galvanometer.

A working mode of the multi-modal imaging device based on Raman spectroscopy and optical coherence tomography as shown in FIG. 2 may be a mode described as follows:

the excitation light from the first light source 101 sequentially passes through the first beam splitting mirror 102 and the co-localization module 300 and enters the first optical fiber 104 after collimated by the first coupling objective lens 103. The emergent light from the first optical fiber 104 passes through the collective lens 115, wherein the first optical fiber is the multi-core optical fiber. Parameters of the collective lens 115 may be selected to control a size of a light spot from Raman spectroscopy detection light, wherein a diameter of the light spot can be adjusted within a range from 5 μm to 1 mm. The target object is detected through the detection window 402 after the emergent light from the collective lens 115 is optically coupled with the imaging detection light from the optical coherence tomography module 200 through the first dichroscope 106. Raman spectroscopy scattering light from the target object is returned along a light path approximately the same as a light path of the excitation light and is reflected by the first beam splitting mirror 102 to enter the grating 107 so as to be split, and the emergent light from the grating 107 is tested through the spectrometer 109 after passing through the receiving lens 108.

After passing through the beam splitter 202, the imaging detection light from the second light source 201 enters the second optical fiber 205 through the other part 204' of the coupling optical fiber 204, and then enters the probe 400. After passing through the coupling adhesive 210, the emergent light from the second optical fiber 205 of the probe 400 enters the second focusing lens 217, and then enters the first reflecting mirror 208 through the diffraction lens 227. Parameters of the second focusing lens 217 may be selected to control a size of a light spot of the imaging detection light, wherein a diameter of the light spot can be adjusted within a range from 5 μm to 1 mm. By using the diffraction lens 227 in the second lens group 207, the imaging resolution is improved. The emergent light from the first reflecting mirror 208 enters the first dichroscope 106 so as to be coupled with the Raman spectroscopy excitation light passing through the first dichroscope 106, and then, the target object is imaged through the detection window 402. In this implementation, the proximal scanning sub-module 209 controls the position of the first reflecting mirror 208 by rotating along at least one axis, and then, a light path reflected by the first reflecting mirror 208 is affected, so that two-dimensional scanning for the target object is achieved. The scattering light from the target object is returned along a light path basically the same as the incident light and is detected by the detector 206 after passing by the beam splitter 202, the interferometer 203, and the circulator (not shown).

In this implementation, by adjusting an angle of a light path between the first flip mirror 301 and the second flip mirror 302 relative to a light path between the first beam splitting mirror 102 and the first coupling objective lens 103, the co-localization module 300 is switchable between the first mode and the second mode.

In the first mode, when the mirror surfaces of the first flip mirror 301 and the second flip mirror 302 are parallel to the light path between the first beam splitting mirror 102 and the first coupling objective lens 103, the existence of the co-localization module 300 does not affect an incident direction of the light path between the first beam splitting mirror 102 and the first coupling objective lens 103, and thus, a sampling position (such as the above-mentioned first sampling position) of the Raman spectroscopy excitation light on the target object is not affected.

In the second mode, when the mirror surfaces of the first flip mirror 301 and the second flip mirror 302 are not parallel to the light path between the first beam splitting mirror 102 and the first coupling objective lens 103, for example, they are arranged at angles shown in FIG. 2, the first flip mirror 301 is configured to receive and reflect light transmitted by the first beam splitting mirror 102, the first scanning galvanometer 303 is configured to receive and reflect reflected light from the first flip mirror 301, the second scanning galvanometer 304 is configured to receive and reflect reflected light from the first scanning galvanometer 303, the second flip mirror 302 is configured to receive and reflect reflected light from the second scanning galvanometer 304, and the first coupling objective lens 103 is configured to receive reflected light from the second flip mirror 302. In such a case, the co-localization module 300 in the second mode will affect the Raman spectroscopy excitation light. For example, by rotating the first scanning galvanometer 303 and/or the second scanning galvanometer 304 around a preset axis, the emergent light from the first beam splitting mirror 102 will be deviated from a direction of an original light path (such as a direction of the light path in the first mode) at a certain angle, which leads to a change of a position of the incident light from the first coupling objective lens 103. As a result, the sampling position (such as the above-mentioned first sampling position) of the Raman spectroscopy excitation light on the target object is changed. In the present implementation, the first scanning galvanometer 303 and the second scanning galvanometer 304 can respectively rotate along axes orthogonal to each other.

However, the present disclosure is not limited thereto, and spatial orientations of the axes for rotating the first scanning galvanometer 303 and the second scanning galvanometer 304 can be set by the skilled in the art on the basis of above disclosure according to an actual situation or as required. An axis with a certain orientation in a given coordinate system can be selected, and thus, a position/angle/shape of the Raman spectroscopy excitation light is affected in different modes by rotating the first scanning galvanometer 303 and the second scanning galvanometer 304. In this implementation, each of the first scanning galvanometer 303 and the second scanning galvanometer 304 adopts the MEMS-driven reflecting mirror. However, the present disclosure is not limited thereto, and other optical elements, such as the Galvo galvanometer or the resonant galvanometer, with the same function can be used by the skilled in the art on the basis of above disclosure according to an actual situation or as required. In addition to the multi-modal imaging device based on Raman spectroscopy and optical coherence tomography shown in FIG. 2, the present disclosure further provides another multi-modal imaging device based on Raman spectroscopy and optical coherence tomography, and next, detailed description therefor will be shown in conjunction with FIG. 4.

Figure 4:
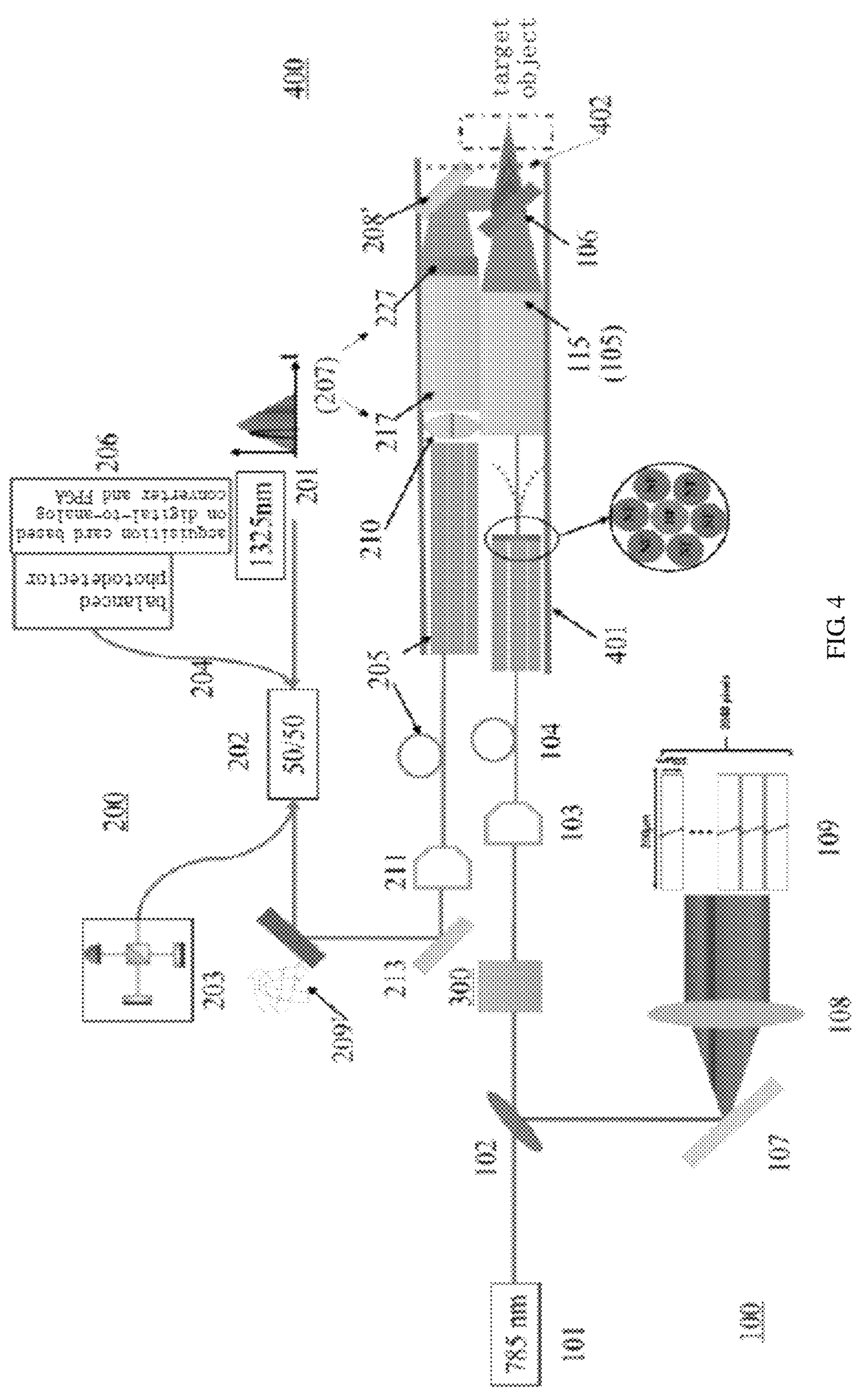
FIG. 4 shows a schematic diagram of a multi-modal imaging device based on Raman spectroscopy and optical coherence tomography according to another implementation of an embodiment of the present disclosure.

FIG. 4 shows a schematic diagram of a multi-modal imaging device based on Raman spectroscopy and optical coherence tomography according to another implementation of an embodiment of the present disclosure.

Refer to FIG. 4, all components and effects and light paths of all the components included in the probe 400, the Raman spectroscopic analysis module 100 and the co-localization module 300 which are included in the multi-modal imaging device based on Raman spectroscopy and optical coherence tomography are consistent with those in FIG. 2, and details thereof refer to the description in FIG. 2 so as not to be repeated herein.

The optical coherence tomography module 200 may include a detector 206, a second light source 201, a beam splitter 202, an interferometer 203, a coupling optical fiber 204, a remote scanning sub-module 209', a first reflecting mirror 213, a second coupling objective lens 211, a second optical fiber 205, a second lens group 207, and a second reflecting mirror 208'.

The second light source 201 may select any light source applicable to optical coherence tomography in the art, for example, a swept light source of which a wavelength is 1325 nm is used in an implementation shown in FIG. 4.

The detector 206 may include a balanced photodetector and an acquisition system based on a high-speed digital-to-analog converter and a Field Programmable Gate Array (FPGA), which can achieve tissue structure image reconstruction and display of a video flow. An FPGA system converts a detection light interference signal into a sample structure grayscale map and an attenuation coefficient grayscale map which are transmitted to an upper computer so as to be displayed.

The beam splitter 202 may be a 50/50 beam splitter as shown in the figure.

A circulator (not shown) may be arranged between the detector 206 and the beam splitter 202.

The beam splitter 202, the remote scanning sub-module 209', the first reflecting mirror 213, the second coupling objective lens 211 and the second optical fiber 205 may be sequentially arranged in a transmission direction of emergent light from the second light source 201.

The second light source 201, the interferometer 203, the detector 206 and the remote scanning sub-module 209' may be optically coupled to the beam splitter 202 via the coupling optical fiber 204.

The remote scanning sub-module 209' may be arranged between the first reflecting mirror 213 and the beam splitter 202 and may be configured to receive and reflect light from the second light source 201 and transmitted by the beam splitter 202.

The second coupling objective lens 211 may be configured to receive light reflected by the first reflecting mirror 213.

The second optical fiber 205 may be configured to receive emergent light from the second coupling objective lens 211.

The second lens group 207 may be configured to receive emergent light from the second optical fiber 205, the second reflecting mirror 208' may be configured to reflect emergent light from the second lens group 207, and the first dichroscope 106 may be configured to reflect reflected light from the second reflecting mirror 208', so that light from the first lens group 105 is coupled with light from the second lens group 207.

The first lens group 105 and the second lens group 207 may be arranged in parallel in the probe 400, and the first dichroscope 106, the second reflecting mirror 108' and at least one part of the second optical fiber 205 may be arranged in the probe 400. By such a design of the probe, an internal diameter of the probe can be reduced to 2-10 mm (which is much smaller than the size of 5 cm used in a traditional light path design in the prior art), which is beneficial to integration into a working channel of an existing endoscope system to reduce damage possibly brought by endoscope detection, thereby being beneficial to clinical application.

The remote scanning sub-module 209' may be configured to control imaging detection light from the second light source 201 by rotating around at least one axis (such as x axis and/or y axis) so as to obtain a position of the tissue structure image of the target object.

The remote scanning sub-module 209' may include a Galvo galvanometer or an MEMS-driven reflecting mirror, wherein the Galvo galvanometer or the MEMS-driven reflecting mirror may receive and reflect light from the beam splitter 202 or light from the first reflecting mirror 213.

The remote scanning sub-module 209' may rotate around at least one axis (such as x axis and/or y axis) to achieve rapid two-dimensional scanning (i.e., line-by-line scanning, one two-dimensional tissue structure image is obtained by scanning every time) for the target object, thereby obtaining at least one two-dimensional tissue structure image of the target object; and when the target object is scanned to obtain a plurality of two-dimensional tissue structure images, a three-dimensional view of the target object can be formed.

The second optical fiber 205 may include a multi-core optical fiber, wherein cores may be arranged according to actual demands (such as a layout mode shown in FIG. 2 to FIG. 4), which is no longer repeated herein.

The second lens group 207 may include a second focusing lens 217 and a diffraction lens 227, wherein the diffraction lens 227 may be arranged between the second focusing lens 217 and the second reflecting mirror 208'.

A coupling adhesive 210 may be arranged between the second optical fiber 205 and the second focusing lens 217, wherein the coupling adhesive 210 may be configured to better couple a light path between the second optical fiber 205 and the second focusing lens 217 so as to better transmit light. It is noted that the coupling adhesive 210 is not necessarily arranged, but is preferably arranged.

By using the second focusing lens 217, a size of a light spot of incident light emitted by the second light source 201 can be controlled. As required, the size of the light spot can be adjusted within a range from 5 μm to 1 mm (diameter). In addition, a usable focusing lens includes a focusing lens with high dispersion and/or a high numerical aperture. For example, the usable focusing lens has an effective focal length of 2-3 mm, a working distance of 1 mm, and a numerical aperture expressed as N/A=0.5. The lens with high dispersion can increase an axial field of view, and the high numerical aperture is beneficial to the improvement of a resolution and an imaging signal-to-noise ratio. In addition, in this implementation of the present disclosure, the diffraction lens 227 can compensate the dispersion, improve a wavelength and a bandwidth, and improve the resolution, thereby improving the imaging quality.

The second optical fiber 205 or the coupling optical fiber 204 may include a single-mode optical fiber.

A working mode of the multi-modal imaging device based on Raman spectroscopy and optical coherence tomography as shown in FIG. 4 may be a mode described as follows:

the excitation light from the first light source 101 sequentially passes through the first beam splitting mirror 102 and the co-localization module 300 and enters the first optical fiber 104 after collimated by the first coupling objective lens 103. The emergent light from the first optical fiber 104 passes through the collective lens 115, wherein the first optical fiber is the multi-core optical fiber. Parameters of the collective lens 115 may be selected to control a size of a light spot from Raman spectroscopy detection light, wherein a diameter of the light spot can be adjusted within a range from 5 μm to 1 mm. The target object is detected through the detection window 402 after the emergent light from the collective lens 115 is optically coupled with the imaging detection light from the optical coherence tomography module 200 through the first dichroscope 106. Raman spectroscopy scattering light from the target object is returned along a light path approximately the same as a light path of the excitation light and is reflected by the first beam splitting mirror 102 to enter the grating 107 so as to be split, and the emergent light from the grating 107 is tested through the spectrometer 109 after passing through the receiving lens 108.

After passing through the beam splitter 202, the imaging detection light from the second light source 201 reaches the remote scanning sub-module 209' through the coupling optical fiber 204, and reaches the first reflecting mirror 213 after reflected by the remote scanning sub-module 209', the imaging detection light reflected by the first reflecting mirror 213 reaches the second coupling objective lens 211, enters the second optical fiber 205 after collimated by the second coupling objective lens 211, and then, enters the probe 400. The emergent light from the second optical fiber 205 in the probe 400 enters the second focusing lens 217 after passing through the coupling adhesive 210, and then enters the second reflecting mirror 208' through the diffraction lens 227. Parameters of the second focusing lens 217 may be selected to control a size of a light spot of the imaging detection light, wherein a diameter of the light spot can be adjusted within a range from 5 μm to 1 mm. By using the diffraction lens 227 in the second lens group 207, the imaging resolution is improved. The emergent light from the second reflecting mirror 208' enters the first dichroscope 106 so as to be coupled with the Raman spectroscopy excitation light passing through the first dichroscope 106, and then, the target object is imaged through the detection window 402. In this implementation, the remote scanning sub-module 209' controls the imaging detection light from the second light source 201 by rotating along at least one axis so as to obtain a position of the tissue structure image of the target object, so that two-dimensional scanning for the target object is achieved. The scattering light from the target object is returned along a light path basically the same as the incident light and is detected by the detector 206 after passing by the second coupling objective lens 211, the first reflecting mirror 213, the remote scanning sub-module 209', the beam splitter 202, the interferometer 203, and the circulator (not shown).

In this implementation, by adjusting an angle of a light path between the first flip mirror 301 and the second flip mirror 302 relative to a light path between the first beam splitting mirror 102 and the first coupling objective lens 103, the co-localization module 300 is switchable between the first mode and the second mode.

In the first mode, when the mirror surfaces of the first flip mirror 301 and the second flip mirror 302 are parallel to the light path between the first beam splitting mirror 102 and the first coupling objective lens 103, the existence of the co-localization module 300 does not affect an incident direction of the light path between the first beam splitting mirror 102 and the first coupling objective lens 103, and thus, a sampling position (such as the above-mentioned first sampling position) of the Raman spectroscopy excitation light on the target object is not affected.

In the second mode, when the mirror surfaces of the first flip mirror 301 and the second flip mirror 302 are not parallel to the light path between the first beam splitting mirror 102 and the first coupling objective lens 103, for example, they are arranged at angles shown in FIG. 4, the first flip mirror 301 is configured to receive and reflect light transmitted by the first beam splitting mirror 102, the first scanning galvanometer 303 is configured to receive and reflect reflected light from the first flip mirror 301, the second scanning galvanometer 304 is configured to receive and reflect reflected light from the first scanning galvanometer 303, the second flip mirror 302 is configured to receive and reflect reflected light from the second scanning galvanometer 304, and the first coupling objective lens 103 is configured to receive reflected light from the second flip mirror 302. In such a case, the co-localization module 300 in the second mode will affect the Raman spectroscopy excitation light. For example, by rotating the first scanning galvanometer 303 and/or the second scanning galvanometer 304 around a preset axis, the emergent light from the first beam splitting mirror 102 will be deviated from a direction of an original light path (such as a direction of the light path in the first mode) at a certain angle, which leads to a change of a position of the incident light from the first coupling objective lens 103. As a result, the sampling position (such as the above-mentioned first sampling position) of the Raman spectroscopy excitation light on the target object is changed. In the present implementation, the first scanning galvanometer 303 and the second scanning galvanometer 304 can respectively rotate along axes orthogonal to each other.

However, the present disclosure is not limited thereto, and spatial orientations of the axes for rotating the first scanning galvanometer 303 and the second scanning galvanometer 304 can be set by the skilled in the art on the basis of above disclosure according to an actual situation or as required. An axis with a certain orientation in a given coordinate system can be selected, and thus, a position/angle/shape of the Raman spectroscopy excitation light is affected in different modes by rotating the first scanning galvanometer 303 and the second scanning galvanometer 304. In this implementation, each of the first scanning galvanometer 303 and the second scanning galvanometer 304 adopts the MEMS-driven reflecting mirror. However, the present disclosure is not limited thereto, and other optical elements, such as the Galvo galvanometer or the resonant galvanometer, with the same function can be used by the skilled in the art on the basis of above disclosure according to an actual situation or as required.

In the implementation shown in FIG. 2 or FIG. 4, the multi-modal imaging device may further include an image processing module (not shown) configured to fuse the Raman spectroscopic information of the first sampling position and the at least one two-dimensional tissue structure image of the second sampling position, which are spatially co-localized, so as to generate fused multi-modal information of the concerned area.

As an example, the image processing module can process the Raman spectroscopic information and the two-dimensional tissue structure image by fusion by using a long short term memory (LSTM) algorithm so as to generate the fused multi-modal information of the concerned area.

In the implementation shown in FIG. 2 or FIG. 4, the multi-modal imaging device provided in the embodiment of the present disclosure has a plurality of operating modes, some of which will be exemplarily listed hereinafter.

Figure 5A:
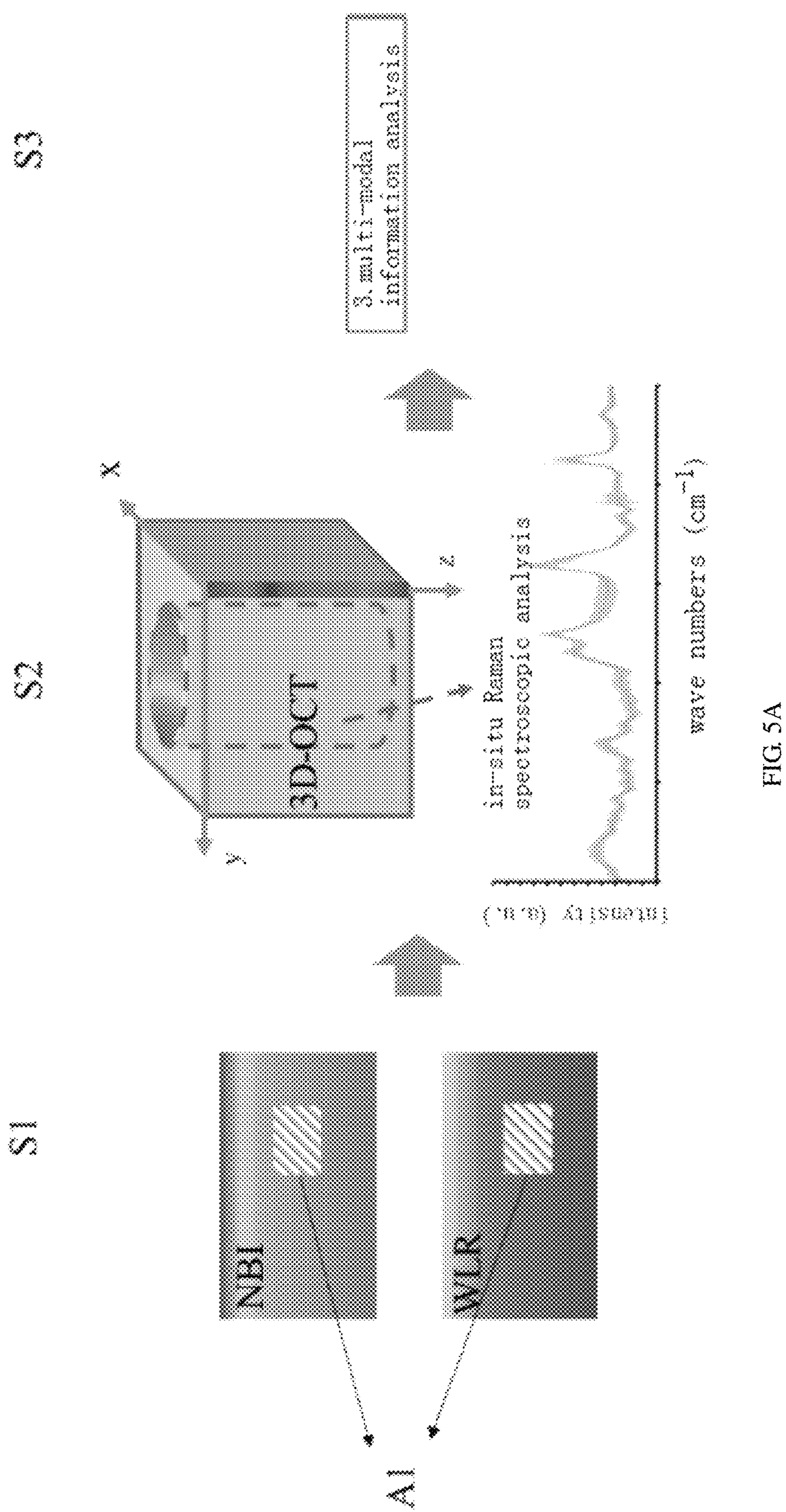
FIG. 5A shows a schematic diagram of a co-localization detection process actually generated during operation of a multi-modal imaging device based on Raman spectroscopy and optical coherence tomography according to an implementation of an embodiment of the present disclosure.

As a first operating mode, a co-localization detection process thereof may refer to FIG. 5A. In this operating mode, by using the second focusing lens 217, a size of a light spot of the optical coherence tomography module 200 on the target object is larger than a size of the first sampling position.

In step S1, the target object is imaged by NBI or WLR, and the concerned area A1 (a shadow part with slashes) is recognized. The recognition process can be performed by operating personnel or a doctor or by means of an algorithm. In a preferred implementation, the concerned area (a tumor or suspected tumor part) is automatically recognized by a deep learning model (CNN) image segmentation algorithm.

In step S2, the first sampling position of the Raman spectroscopic analysis module 100 is moved by the co-localization module 300 so as to basically overlap with the concerned area A1, and Raman spectroscopic analysis is performed on the area; the Raman spectroscopic information can reflect structural information, such as lipid and proteins, of specific molecules, and a signal intensity is related to a concentration; and therefore, the selection of the specific molecules related to the occurrence of cancer lesion is very beneficial to cancer screening and test. Next, the optical coherence tomography module 200 performs line-by-line scanning imaging in the first sampling position by using the proximal scanning sub-module 209 or the remote scanning sub-module 209' to obtain the at least one two-dimensional tissue structure image spatially co-localized with the first sampling position, and the at least one two-dimensional tissue structure image is wholly a 3D-OCT image on the sampling position.

In step S3, the obtained multi-modal information which is spatially co-localized is analyzed. Preferably, analysis is performed by fusion by using the LSTM algorithm. Thus, it can be seen that the multi-modal imaging device in the present disclosure controls the first sampling position of the Raman spectroscopic analysis module 100 by using the co-localization module 300 to basically overlap with the concerned area, and performs scanning imaging in this area by using the optical coherence tomography module 200, which allows to obtain the Raman spectroscopic information and tissue structure image information which are spatially co-localized. Due to high spatial consistency, the multi-modal information of the same precise position in the true sense is obtained in the present disclosure, which is beneficial to improvement of the correlation between the Raman spectroscopic information and the tissue structure image information, thereby improving the accuracy and efficiency of diagnosis/screening. It is expected to point out that the present disclosure is not limited to such one specific implementation, for example, although it is not shown, the co-localization module 300 in the present disclosure can also control the second sampling position of the optical coherence tomography module 200 to move to basically overlap with the concerned area A1, and the sampling position is analyzed and detected by using the Raman spectroscopic analysis module 100, so that spatial co-localization is achieved in the concerned area.

Figure 5B:
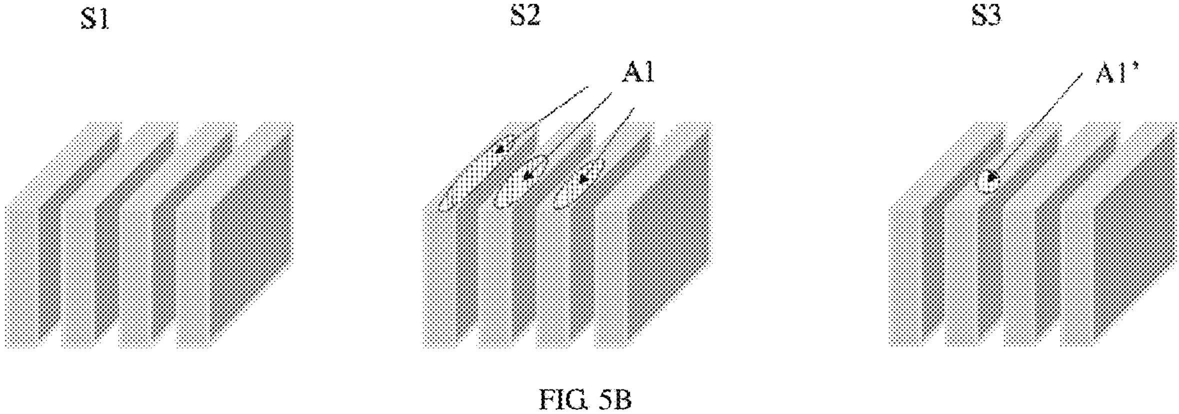
FIG. 5B shows a schematic diagram of another co-localization detection process actually generated during operation of a multi-modal imaging device based on Raman spectroscopy and optical coherence tomography according to an implementation of an embodiment of the present disclosure.

As another operating mode, a co-localization detection process thereof may refer to FIG. 5B. In this mode, the first lens group 105 in the Raman spectroscopic analysis module 100 adopts a focusing lens, and the size of the first sampling position is smaller than the size of the light spot of the optical coherence tomography module 200 on the target object. In this mode, the optical coherence tomography module 200 is configured to obtain the at least one two-dimensional tissue structure image of the target object by using the imaging detection light and determine the concerned area of the target object in the at least one two-dimensional tissue structure image, and the co-localization module 300 is configured to control the first sampling position of the excitation light in the Raman spectroscopic analysis module 100 according to the determined concerned area, thereby obtaining the Raman spectroscopic information of different positions in the concerned area.

Specifically, in step S1, the at least one two-dimensional tissue structure image (FIG. 5 shows four two-dimensional tissue structure images of the target object, which are wholly similar to a 3D-OCT image corresponding to the target object) of the target object is obtained after line-by-line scanning performed by the proximal scanning sub-module 209 or the remote scanning sub-module 209'.

In step S2, the concerned area A1 (a shadow part with slashes) is recognized for each two-dimensional tissue structure image. The recognition process can be performed by operating personnel or a doctor or by means of an algorithm.

In step S3, the sampling position A1' (a shadow part with slashes) of the Raman spectroscopic analysis module is controlled by the co-localization module 300, thereby obtaining the Raman spectroscopic information in the concerned area A1. The Raman spectroscopic information can reflect structural information, such as lipid and proteins, of specific molecules, and a signal intensity is related to a concentration; and therefore, the selection of the specific molecules related to the occurrence of cancer lesion is very beneficial to cancer screening and test. According to the embodiment of the present disclosure, the multi-modal information (OCT tissue structure image and co-localized Raman spectroscopy data) can be fused by using the LSTM algorithm, which can further improve the accuracy of cancer or tumor diagnosis. Thus, it can be seen that the co-localization module 300 achieves high-efficiency cooperative operation of Raman spectroscopic analysis and optical coherence tomography by controlling the sampling position of the Raman spectroscopy excitation light in the specific concerned area, so that high-accuracy and high-specificity screening and diagnosis for cancers/tumors can be achieved. As mentioned above, the present disclosure is not limited thereto, it is also possible that the concerned area A1 is obtained by using the Raman spectroscopic analysis module 100 by means of an appropriate lens and operating mode, and the optical coherence tomography module 200 is controlled to scan in the concerned area A1 to obtain the Raman spectroscopic information and the tissue structure image information which are spatially co-localized. Such a mode has the advantages that the concerned area can be obtained based on two-dimensional Raman spectroscopic information, and the corresponding axial tissue structure image information is further obtained by using 3D-OCT imaging. The skilled in the art can select a specific corresponding implementation on the basis of the above-mentioned disclosed contents according to different concerns.

The multi-modal imaging device based on Raman spectroscopy and optical coherence tomography according to the embodiment of the present disclosure can be used in test scenarios of glioma, thyroid tumor, cervical cancer, bladder cancer, prostate cancer, gynecological tumor, urinary tumor and the like to realize the test of transverse planar incisal edges of tissues.

The multi-modal imaging device based on Raman spectroscopy and optical coherence tomography as shown in FIG. 1, FIG. 2 or FIG. 4 may be an endoscope.

A diameter of the probe shown in FIG. 1, FIG. 2 or FIG. 4 may be 2-10 mm.

A diameter of the probe shown in FIG. 1, FIG. 2 or FIG. 4 may be 2-5 mm.

In the multi-modal imaging device based on Raman spectroscopy and optical coherence tomography as shown in FIG. 2 or FIG. 4, exemplary technical parameters of the optical coherence tomography module and the Raman spectroscopic analysis module can be shown as follows:

the technical parameters of the optical coherence tomography module may include: an imaging speed is 2-5 volume imaging/s or 200-500 B-scan frame/s, an imaging field of view is 0.5 mm to 2 mm, and a resolution and an imaging depth depend on a central wavelength of a light source; if the central wavelength is 1325 nm, the resolution is 15-20 μm, and the depth is 1-2 mm; and if the central wavelength is 800 nm, the resolution is 4-10 μm, and the depth is 0.5-1 mm.

The technical parameters of the Raman spectroscopic analysis module may include: a spectroscopic acquisition speed is 2-5 Hz, a spectroscopic resolution is 5-10 wave numbers, a range of a wavelength received by the spectrometer is 800-1100 nm, and a Raman spectroscopy detection range is 800-1800 wave numbers and 2800-3600 wave numbers.

It is noted that above parameters are only exemplary and may also be other parameters as long as these parameters can achieve the above-mentioned multi-modal imaging device based on Raman spectroscopy and optical coherence tomography and corresponding technical effects.

The multi-modal imaging device based on Raman spectroscopy and optical coherence tomography in the present disclosure is described in detail above in conjunction with the two implementations in FIG. 1 to FIG. 5B. It can be known from the above-mentioned detailed description that the optical coherence tomography module in the multi-modal imaging device based on Raman spectroscopy and optical coherence tomography in the present disclosure is configured to obtain the at least one two-dimensional tissue structure image of the target object, and the co-localization module is configured to control the first sampling position of the excitation light in the Raman spectroscopic analysis module and/or the second sampling position in the optical coherence tomography module according to the determined concerned area, so that the first sampling position and the second sampling position are spatially co-localized in the concerned area. By such cooperative operation, operating personnel are allowed to preliminarily affirm, according to the tissue structure image, the concerned area where a cancer risk is suspected, and next, the co-localization module guides and controls the sampling positions of the Raman spectroscopic analysis module and/or the optical coherence tomography module, thereby obtaining the Raman spectroscopic information of the concerned area, and obtaining more accurate information serving as a diagnosis basis according to the advantages of high accuracy and specificity of Raman spectroscopy. The concerned area can be determined according to an algorithm or experience of the operating personnel. In a preferred implementation, the concerned area is rapidly and automatically recognized according to the algorithm, and then, the co-localization module guides the excitation light from the Raman spectroscopic analysis module and/or the detection light from the optical coherence tomography module to the sampling positions, thereby obtaining relatively accurate spectroscopic information of the specific molecules (such as lipid and proteins) related to cancers/tumors, which serves as a diagnosis basis; and in the implementation, the process from recognizing the concerned area to guiding the Raman spectroscopy excitation light through the co-localization module can be automatized, which allows in-vivo real-time and precise cancer test.

In above process, the co-localization module can reduce areas which need to be tested by Raman spectroscopic analysis, that is to say, it is unnecessary to perform Raman spectroscopic analysis on all areas, but only the concerned area is analyzed, which avoids the defect of low test speed of Raman spectroscopic analysis to a great extent, however, the advantages of high accuracy and specificity of Raman spectroscopic analysis are still utilized, so that the overall test efficiency is increased.

In addition, the co-localization module is switchable between the two modes, so that a co-localization function can be enabled and disabled as required.

Besides, by disposing the probe of the multi-modal imaging device based on Raman spectroscopy and optical coherence tomography, the size of the probe can be reduced, for example, the size of the probe can be reduced to 2-10 mm and even 2-5 mm, which is beneficial to integration into a working channel of an existing endoscope system, thereby being beneficial to clinical application.

Finally, with cervical cancer mentioned in the background art as an example, when the multi-modal imaging device based on Raman spectroscopy and optical coherence tomography in the present disclosure is used as an endoscope for diagnosis, it can be obtained in a cooperative, efficient, non-invasive and real-time mode that the sensitivity and the specificity of diagnosis for CIN are higher than 98%, and the accuracy of diagnosis for CINI early precancerous lesions is higher than 90%.

Besides, a control method for the multi-modal imaging device based on Raman spectroscopy and optical coherence tomography according to an embodiment of the present disclosure may be recorded in a computer-readable recording medium. Specifically, according to the present disclosure, a computer-readable recording medium having a computer-executable instruction stored thereon can be provided, and the processor, when executing the computer-executable instruction, performs the control method for the above-mentioned multi-modal imaging device based on Raman spectroscopy and optical coherence tomography. Examples of the computer-readable recording medium may include a magnetic medium (such as a hard disk, a floppy disk, and a magnetic tape); an optical medium (such as a CD-ROM and a DVD); a magnetic-optical medium (such as a compact disc); and a particularly prepared hardware device (such as a read-only memory (ROM), a random access memory (RAM), and a flash memory) configured to store and execute program instructions.

Besides, according to the present disclosure, equipment including a processor and a memory can be further provided. Computer-executable instructions are stored in the memory, wherein the processor, when executing the computer-executable instructions, performs the above-mentioned control method. Examples of the computer-executable instructions include machine codes generated by a compiler and files including advanced codes that can be executed by a computer by using an interpreter.

It should be noted that flow diagrams and block diagrams in the accompanying drawings illustrate possibly achieved system architectures, functions, and operations of systems, methods, and computer program products according to various implementations of the present disclosure. In view of this point, each box in the flow diagrams or block diagrams can represent a module, a program segment, or a part of the codes, and the module, the program segment, or a part of the codes includes at least one executable instruction for achieving a specified logical function. It should be also noted that, in some implementations as substitutions, functions marked in the box can also occur in a different order than that marked in the accompanying drawings. For example, two consecutively-represented boxes can be actually executed in parallel basically, and they can sometimes be executed in an opposite order, which depends on an involved function. It should be also noted that each box in the block diagrams and/or the flow diagrams and combinations of the boxes in the block diagrams and/or the flow diagrams can be achieved by using a special-purpose hardware-based system that performs specified functions or operations, or can be achieved by using a combination of special-purpose hardware and computer instructions.

Generally speaking, the various disclosed exemplary embodiments or implementations can be implemented in hardware or a special-purpose circuit, software, firmware, logic or any combinations thereof. Some aspects can be implemented in hardware, and other aspects can be implemented in firmware or software that can be executed by a controller, a microprocessor, or other computing equipment. When various aspects of the embodiment of the present disclosure are illustrated or described as block diagrams and flow diagrams, or represented by some other graphics, it is understood that the boxes, device, system, technology, or method described herein can be implemented as non-restrictive examples in hardware, software, firmware, a special-purpose circuit or logic, general-purpose hardware or a controller or other computing equipment, or some combinations thereof.

The implementations of the exemplary embodiments of the present disclosure described in detail above are only illustrative, rather than restrictive. It should be understood by those skilled in the art that various modifications and combinations can be performed on these embodiments or features thereof without departing from the principle and spirit of the present disclosure, and such modifications shall fall within the scope of the present disclosure.

What is claimed is:

1. A multi-modal imaging device based on Raman spectroscopy and optical coherence tomography, comprising:

a Raman spectroscopic analysis module, configured to obtain Raman spectroscopic information of a target object at a first sampling position by using excitation light;

an optical coherence tomography module, configured to obtain at least one two-dimensional tissue structure image of the target object at a second sampling position by using imaging detection light; and a co-localization module, configured to control at least one of the first sampling position of the excitation light in the Raman spectroscopic analysis module or the second sampling position in the optical coherence tomography module according to a determined concerned area of the target object, so that the first sampling position and the second sampling position are spatially co-localized in the determined concerned area, wherein the co-localization module is further configured to:

control the first sampling position of the excitation light in the Raman spectroscopic analysis module to move to overlap with the determined concerned area, and perform imaging detection on the determined concerned area by using the optical coherence tomography module, so that the first sampling position and the second sampling position are spatially co-localized in the determined concerned area; or control the second sampling position in the optical coherence tomography module to move to overlap with the determined concerned area, and analyze and detect the determined concerned area by using the Raman spectroscopic analysis module, so that the first sampling position and the second sampling position are spatially co-localized in the determined concerned area; or control the first sampling position and the second sampling position at least one of simultaneously or synchronously to scan, analyze and detect the determined concerned area, so that the first sampling position and the second sampling position are spatially co-localized in the determined concerned area, wherein the multi-modal imaging device comprises a probe provided with a shell and a detection window and configured to detect the target object, and the excitation light from the Raman spectroscopic analysis module and the imaging detection light from the optical coherence tomography module are coupled in the probe, wherein the Raman spectroscopic analysis module comprises a first light source, a first beam splitting mirror, a first coupling objective lens, a first optical fiber, a spectrometer, a first lens group, and a first dichroscope, wherein the first beam splitting mirror is configured to transmit the excitation light from the first light source and reflect Raman spectroscopy scattering signal light from the target object, wherein the spectrometer is configured to receive the Raman spectroscopy scattering signal light from the target object reflected by the first beam splitting mirror, wherein the first coupling objective lens is configured to receive emergent light from the first beam splitting mirror or the co-localization module, wherein the first optical fiber is configured to receive emergent light from the first coupling objective lens, wherein the first lens group is configured to receive emergent light from the first optical fiber, wherein the first lens group comprises a collective lens, and wherein the first dichroscope is configured to receive and transmit emergent light from the first lens group.

2. The multi-modal imaging device based on Raman spectroscopy and optical coherence tomography according to claim 1, wherein a grating and a receiving lens are arranged between the spectrometer and the first beam splitting mirror, the grating is configured to split reflected light from the first beam splitting mirror, the receiving lens is configured to receive emergent light from the grating, and the spectrometer is configured to receive emergent light from the receiving lens.

3. The multi-modal imaging device based on Raman spectroscopy and optical coherence tomography according to claim 1, wherein the first optical fiber comprises a multi-core optical fiber, a central fiber core group consisting of at least one fiber core of a central part of the multi-core optical fiber is configured to transmit Raman spectroscopy excitation light from the first light source, and peripheral fiber core groups consisting of at least one fiber core surrounding the central fiber core group of the multi-core optical fiber are configured to transmit the Raman spectroscopy scattering signal light.

4. The multi-modal imaging device based on Raman spectroscopy and optical coherence tomography according to claim 3, wherein a band-pass fiber is arranged on a tail end of a side, close to the target object, of the central fiber core group, and at least one of notch filters or long pass filters are arranged on tail ends of sides, close to the target object, of the peripheral fiber core groups.

5. The multi-modal imaging device based on Raman spectroscopy and optical coherence tomography according to claim 1, wherein the optical coherence tomography module comprises a detector, a second light source, a beam splitter, an interferometer, a coupling optical fiber, a second optical fiber, a second lens group, a proximal scanning sub-module, and a first reflecting mirror;

the second light source, the interferometer, the detector and the second optical fiber are optically coupled to the beam splitter via a first part of the coupling optical fiber;

a second part of the coupling optical fiber is coupled to the second optical fiber;

the second lens group is configured to receive emergent light from the second optical fiber, the first reflecting mirror is configured to reflect emergent light from the second lens group, and the first dichroscope is configured to reflect reflected light from the first reflecting mirror, so that light from the first lens group is coupled with light from the second lens group; and the proximal scanning sub-module is configured to control a position of the first reflecting mirror.

6. The multi-modal imaging device based on Raman spectroscopy and optical coherence tomography according to claim 5, wherein the first lens group and the second lens group are arranged in parallel in the probe, and the first dichroscope, the proximal scanning sub-module, the first reflecting mirror and at least one part of the second optical fiber are arranged in the probe.

7. The multi-modal imaging device based on Raman spectroscopy and optical coherence tomography according to claim 6, wherein the proximal scanning sub-module is configured to control imaging detection light from the second light source by controlling the position of the first reflecting mirror to obtain a position of the at least one two-dimensional tissue structure image of the target object, and wherein the proximal scanning sub-module comprises a micromotor.

8. The multi-modal imaging device based on Raman spectroscopy and optical coherence tomography according to claim 5, wherein the second lens group comprises a second focusing lens and a diffraction lens, and the diffraction lens is arranged between the second focusing lens and the first reflecting mirror.

9. The multi-modal imaging device based on Raman spectroscopy and optical coherence tomography according to claim 1, wherein the optical coherence tomography module comprises a detector, a second light source, a beam splitter, an interferometer, a coupling optical fiber, a remote scanning sub-module, a first reflecting mirror, a second coupling objective lens, a second optical fiber, a second lens group, and a second reflecting mirror;

wherein the beam splitter, the remote scanning sub-module, the first reflecting mirror, the second coupling objective lens and the second optical fiber are sequentially arranged in a transmission direction of emergent light from the second light source;

the second light source, the interferometer, the detector and the remote scanning sub-module are optically coupled to the beam splitter via the coupling optical fiber;

the remote scanning sub-module is arranged between the first reflecting mirror and the beam splitter and is configured to receive and reflect light from the second light source and transmitted by the beam splitter;

the second coupling objective lens is configured to receive light reflected by the first reflecting mirror;

the second optical fiber is configured to receive emergent light from the second coupling objective lens; and the second lens group is configured to receive emergent light from the second optical fiber, the second reflecting mirror is configured to reflect emergent light from the second lens group, and the first dichroscope is configured to reflect reflected light from the second reflecting mirror, so that light from the first lens group is coupled with light from the second lens group.

10. The multi-modal imaging device based on Raman spectroscopy and optical coherence tomography according to claim 9, wherein the first lens group and the second lens group are arranged in parallel in the probe, and the first dichroscope, the second reflecting mirror and at least one part of the second optical fiber are arranged in the probe, wherein the remote scanning sub-module is configured to control imaging detection light from the second light source by rotating around at least one axis to obtain a position of the at least one two-dimensional tissue structure image of the target object, wherein the remote scanning sub-module comprises a Galvo galvanometer, a micro-electromechanical systems driven (MEMS-driven) reflecting mirror or a resonant galvanometer, wherein the second lens group comprises a second focusing lens and a diffraction lens, and the diffraction lens is arranged between the second focusing lens and the second reflecting mirror.

11. The multi-modal imaging device based on Raman spectroscopy and optical coherence tomography according to claim 1, wherein the co-localization module is arranged in an incident light path of the excitation light from the Raman spectroscopic analysis module, wherein the co-localization module is arranged between the first beam splitting mirror and the first coupling objective lens.

12. The multi-modal imaging device based on Raman spectroscopy and optical coherence tomography according to claim 11, wherein the co-localization module has a first mode and a second mode which are switchable;

in the first mode, the co-localization module is configured to not change the first sampling position; and in the second mode, the co-localization module is configured to control the first sampling position.

13. The multi-modal imaging device based on Raman spectroscopy and optical coherence tomography according to claim 12, wherein the co-localization module comprises a first flip mirror, a second flip mirror, a first scanning galvanometer, and a second scanning galvanometer; the first flip mirror and the second flip mirror are arranged between the first beam splitting mirror and the first coupling objective lens;

the first flip mirror and the second flip mirror are configured to control mirror surfaces of the first flip mirror and the second flip mirror to be parallel or not parallel to a light path between the first beam splitting mirror and the first coupling objective lens by rotating around an axis orthogonal to the light path between the first beam splitting mirror and the first coupling objective lens; and the first scanning galvanometer and the second scanning galvanometer are configured to control the first sampling position by rotating around different axes;

wherein in the first mode, the mirror surfaces of the first flip mirror and the second flip mirror are parallel to the light path between the first beam splitting mirror and the first coupling objective lens; and in the second mode, the mirror surfaces of the first flip mirror and the second flip mirror are not parallel to the light path between the first beam splitting mirror and the first coupling objective lens.

14. The multi-modal imaging device based on Raman spectroscopy and optical coherence tomography according to claim 13, wherein in the second mode, the first flip mirror is configured to receive and reflect light transmitted by the first beam splitting mirror, the first scanning galvanometer is configured to receive and reflect reflected light from the first flip mirror, the second scanning galvanometer is configured to receive and reflect reflected light from the first scanning galvanometer, the second flip mirror is configured to receive and reflect reflected light from the second scanning galvanometer, and the first coupling objective lens is configured to receive reflected light from the second flip mirror.

15. The multi-modal imaging device based on Raman spectroscopy and optical coherence tomography according to claim 1, wherein the co-localization module is configured to move the first sampling position to overlap with a position of the determined concerned area.

16. The multi-modal imaging device based on Raman spectroscopy and optical coherence tomography according to claim 1, wherein the first lens group is configured to enable a light spot of the excitation light from the Raman spectroscopic analysis module on the first sampling position overlaps with the determined concerned area.

17. The multi-modal imaging device based on Raman spectroscopy and optical coherence tomography according to claim 1, wherein the multi-modal imaging device is an endoscope.

18. The multi-modal imaging device based on Raman spectroscopy and optical coherence tomography according to claim 1, further comprising:

an image processing module configured to fuse the Raman spectroscopic information of the first sampling position and the at least one two-dimensional tissue structure image of the second sampling position, which are spatially co-localized, so as to generate fused multi-modal information of the determined concerned area.

* * * * *